US00PP27266P2

(12) United States Plant Patent
Oliver

(10) Patent No.: US PP27,266 P2
(45) Date of Patent: Oct. 11, 2016

(54) ***PHLOX* PLANT NAMED 'ZENITH'**

(50) Latin Name: ***Phlox carolina*×*Phlox maculata***
Varietal Denomination: Zenith

(71) Applicant: Charles G. Oliver, Scottdale, PA (US)

(72) Inventor: Charles G. Oliver, Scottdale, PA (US)

( * ) Notice: Subject to any disclaimer, the term of this patent is extended or adjusted under 35 U.S.C. 154(b) by 82 days.

(21) Appl. No.: 14/544,215

(22) Filed: Dec. 9, 2014

(51) Int. Cl.
*A01H 5/00* (2006.01)

(52) U.S. Cl.
USPC ..... Plt./320

(58) Field of Classification Search
USPC ..... Plt./320
See application file for complete search history.

*Primary Examiner* — Annette Para
(74) *Attorney, Agent, or Firm* — C. A. Whealy

(57) ABSTRACT

A new and distinct *Phlox* plant named 'Zenith', characterized by its upright and mounding plant form; vigorous growth habit; freely basal branching habit; early and freely flowering habit; large rounded inflorescences with large pink-colored flowers; and resistance to Powdery Mildew.

2 Drawing Sheets

Botanical designation: *Phlox carolina*×*Phlox maculata.*
Cultivar denomination: 'ZENITH'.

BACKGROUND OF THE INVENTION

The present invention relates to a new and distinct *Phlox* plant, botanically known as *Phlox carolina*×*Phlox maculata* and hereinafter referred to by the name 'Zenith'.

The new *Phlox* plant is a product of a planned breeding program conducted by the Inventor in Upper Tyrone Township, Pa. The objective of the breeding program is to create new vigorous *Phlox* plants with early flowering habit, attractive leaf and flower coloration and resistance to Powdery Mildew.

The new *Phlox* plant originated from an open-pollination in May, 2008 of *Phlox carolina*×*Phlox maculata* 'Daughter of Pearl', disclosed in a U.S. Plant patent application Ser. No. 14/544,219, as the female, or seed, parent with an unknown selection of *Phlox*×*hybrida* as the male, or pollen, parent. The new *Phlox* plant was discovered and selected by the Inventor as a single flowering plant within the progeny of the stated open-pollination in a controlled environment in Upper Tyrone Township, Pa. in June, 2009.

Asexual reproduction of the new *Phlox* plant by vegetative stem cuttings in a controlled greenhouse environment in Upper Tyrone Township, Pa. since September, 2009 has shown that the unique features of this new *Phlox* plant are stable and reproduced true to type in successive generations.

SUMMARY OF THE INVENTION

Plants of the new *Phlox* plant have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Zenith'. These characteristics in combination distinguish 'Zenith' as a new and distinct *Phlox* plant:

1. Upright and mounding plant form.
2. Vigorous growth habit.
3. Freely basal branching habit.
4. Early and freely flowering habit.
5. Large rounded inflorescences with large pink-colored flowers.
6. Resistance to Powdery Mildew.

Plants of the new *Phlox* differ from plants of the female parent, 'Daughter of Pearl', in the following characteristics:

1. Plants of the new *Phlox* are shorter than plants of 'Daughter of Pearl'.
2. Plants of the new *Phlox* have larger and glossier leaves than plants of 'Daughter of Pearl'.
3. Inflorescences of plants of the new *Phlox* are rounded or dome-shaped whereas inflorescences of plants of 'Daughter of Pearl' are conical in shape.
4. Plants of the new *Phlox* have larger flowers than plants of 'Daughter of Pearl'.
5. Plants of the new *Phlox* and 'Daughter of Pearl' differ in flower color as plants of 'Daughter of Pearl' have white and purple-colored flowers.

Plants of the new *Phlox* can be compared to plants of *Phlox carolina* 'Minnie Pearl', not patented. In side-by-side comparisons, plants of the new *Phlox* and 'Minnie Pearl' differed in the following characteristics:

1. Plants of the new *Phlox* were taller than plants of 'Minnie Pearl'.
2. Plants of the new *Phlox* were not as outwardly spreading and loose in plant habit as plants of 'Minnie Pearl'.
3. Plants of the new *Phlox* had glossier and larger leaves than plants of 'Minnie Pearl'.
4. Inflorescences of plants of the new *Phlox* were rounded or dome-shaped whereas inflorescences of plants of 'Minnie Pearl' were flat-topped.
5. Plants of the new *Phlox* had slightly larger flowers than plants of 'Minnie Pearl'.
6. Plants of the new *Phlox* and 'Minnie Pearl' differed in flower color as plants of 'Minnie Pearl' had white-colored flowers.

Plants of the new *Phlox* can also be compared to plants of *Phlox carolina* 'Kim', not patented. In side-by-side comparisons, plants of the new *Phlox* and 'Kim' differed in the following characteristics:

1. Plants of the new *Phlox* were taller than plants of 'Kim'.
2. Plants of the new *Phlox* were not as outwardly spreading as plants of 'Kim'.
3. Plants of the new *Phlox* had glossier and broader leaves than plants of 'Kim'.
4. Flowers of plants of the new *Phlox* were rounded with imbricate petals whereas flowers of plants of 'Kim' were not rounded and petals were not imbricate.
5. Plants of the new *Phlox* had larger flowers than plants of 'Kim'.

BRIEF DESCRIPTION OF THE PHOTOGRAPHS

The accompanying colored photographs illustrate the overall appearance of the new *Phlox* plant showing the colors as true as it is reasonably possible to obtain in colored reproductions of this type. Colors in the photographs may differ slightly from the color values cited in the detailed botanical description which accurately describe the colors of the new *Phlox* plant.

The photograph on the first sheet comprises a side perspective view of typical flowering plants of 'Zenith'.

The photograph at the top of the sheet is a close-up view of a typical flowering plant of 'Zenith'.

DETAILED BOTANICAL DESCRIPTION

The aforementioned photographs and following observations, measurements and values describe plants grown during the spring and summer in one-gallon containers in a polyethylene-covered greenhouse and an outdoor nursery in Upper Tyrone Township, Pa. and under cultural practices typical of *Phlox* production. During the production of the plants, day temperature averaged 26° C. and night temperatures averaged 15° C. Plants were two years old when the photographs and description were taken. In the following description, color references are made to The Royal Horticultural Society Colour Chart, 1995 Edition, except where general terms of ordinary dictionary significance are used.

Botanical classification: *Phlox carolina*×*Phlox maculata* 'Zenith'.

Parentage:

*Female, or seed, parent.*—*Phlox carolina*×*Phlox maculata* 'Daughter of Pearl', disclosed in U.S. Plant Patent application filed concurrently.

*Male, or pollen, parent.*—Unknown selection of *Phlox*×*hybrida*, not patented.

Propagation:

*Type.*—By stem cuttings.

*Time to initiate roots, summer.*—About three weeks at night temperatures about 15° C. and day temperatures about 26° C.

*Time to produce a rooted plant, summer.*—About six weeks at night temperatures about 15° C. and day temperatures about 26° C.

*Root description.*—Medium in thickness, fibrous; white in color.

*Rooting habit.*—Freely branching; medium density.

Plant description:

*Plant and growth habit.*—Herbaceous perennial; upright and mounding plant habit, columnar; vigorous growth habit; freely basal branching habit with about six to eight primary laterals developing per plant; relatively short internodes.

*Plant height.*—About 75 cm.

*Plant width (spread).*—About 30 cm.

*Lateral branches.*—Length: About 60 cm. Diameter: About 3 mm. Internode length: About 4 cm to 6 cm; distally, close to 12 cm. Strength: Strong. Texture: Smooth, glabrous. Color: Close to 144B, mottled and streaked with close to 184B.

Leaf description:

*Arrangement.*—Opposite, simple; sessile.

*Length.*—About 3 cm to 8.5 cm.

*Width.*—About 1 cm to 2.7 cm.

*Shape.*—Lanceolate to obovate.

*Apex.*—Acute.

*Base.*—Abruptly tapering.

*Margin.*—Entire.

*Texture, upper surface.*—Glabrous; thick; glossy; waxy.

*Texture, lower surface.*—Glabrous; thick; waxy.

*Venation pattern.*—Pinnate.

*Color.*—Developing and fully expanded leaves, upper surface: Close to 144A; venation, close to 144A. Developing and fully expanded leaves, lower surface: Close to 144C; venation, close to 144C.

Flower description:

*Flower form and flowering habit.*—Single rotate and salverform flowers arranged in terminal compound panicles; panicles rounded and dome-shaped; freely flowering habit with about 50 to 60 flowers developing per inflorescence; flowers face upright to outwardly.

*Fragrance.*—Moderately fragrant; sweet.

*Natural flowering season.*—Early flowering habit, plants begin flowering about six weeks after planting; plants flowering continuously from May to June in Pennsylvania.

*Postproduction longevity.*—Flowers last about seven to ten days on the plant and as a cut flower; flowers not persistent.

*Flower buds.*—Height: About 2.8 cm. Diameter: About 4 mm. Shape: Elongated oblong. Color: Close to 74C; towards the base, close to 75C.

*Inflorescence height.*—About 9 cm.

*Inflorescence diameter.*—About 10 cm to 12 cm.

*Flower diameter.*—About 3.2 cm.

*Flower depth.*—About 2.8 cm.

*Flower throat diameter.*—About 1.8 mm.

*Flower tube length.*—About 2.8 cm.

*Flower tube diameter, at base.*—About 1.5 mm.

*Petals.*—Quantity per flower and arrangement: Typically five in a single whorl; petals fused at the base into a narrow tube. Lobe length: About 1.4 cm. Lobe width: About 1.7 cm. Shape: Rhomboidal. Apex: Rounded. Margin: Entire, undulate. Texture: Petal lobes, upper and lower surfaces: Smooth, glabrous. Throat: Smooth, glabrous. Tube: Smooth, glabrous. Color: Developing and fully expanded petal lobes, upper surface: Close to 74C; towards the base, close to 155D; color becoming closer to 75D with development. Developing and fully expanded petal lobes, lower surface: Close to 75D. Flower throat: Close to 74C. Flower tube: Close to 74D.

*Sepals*.—Quantity per flower and arrangement: Typically five in a single whorl, fused towards the base into a slender tube. Length: About 7 mm. Width: About 1.5 mm. Shape: Lanceolate. Apex: Acute. Margin: Entire, membraneous. Texture, upper and lower surfaces: Smooth, glabrous. Color, upper and lower surfaces: Close to 145B.

*Peduncles*.—Length: About 4 cm. Diameter: About 2 mm. Angle: Erect. Strength: Strong. Texture: Pilose. Color: Close to 144B.

*Pedicels*.—Length: About 2 mm to 4 mm. Diameter: About 0.7 mm. Angle: About 30° from peduncle axis. Strength: Strong. Texture: Pubescent. Color: Close to 144B.

*Reproductive organs*.—Stamens: Quantity per flower: Typically five. Filament length: About 1.5 mm. Anther shape: Oval. Anther length: About 2 mm. Anther color: Close to 17A. Pollen amount: None observed. Pistils: Quantity per flower: One. Pistil length: About 2.6 cm. Stigma shape: Tri-parted. Stigma color: Close to 154D. Style length: About 2.3 cm. Style color: Close to 154D. Ovary color: Close to 145B.

*Seeds and fruits*.—Seed and fruit development have not been observed on plants of the new *Phlox* plant.

Disease & pest resistance: Plants of the new *Phlox* have been observed to be resistant to Powdery Mildew. Plants of the new *Phlox* have not been observed to be resistant to pests and other pathogens common to *Phlox* plants.

Garden performance: Plants of the new *Phlox* have been observed to have good garden performance and tolerate rain and wind and to temperatures ranging from about −30° C. to 45° C.

It is claimed:

1. A new and distinct *Phlox* plant named 'Zenith' as illustrated and described.

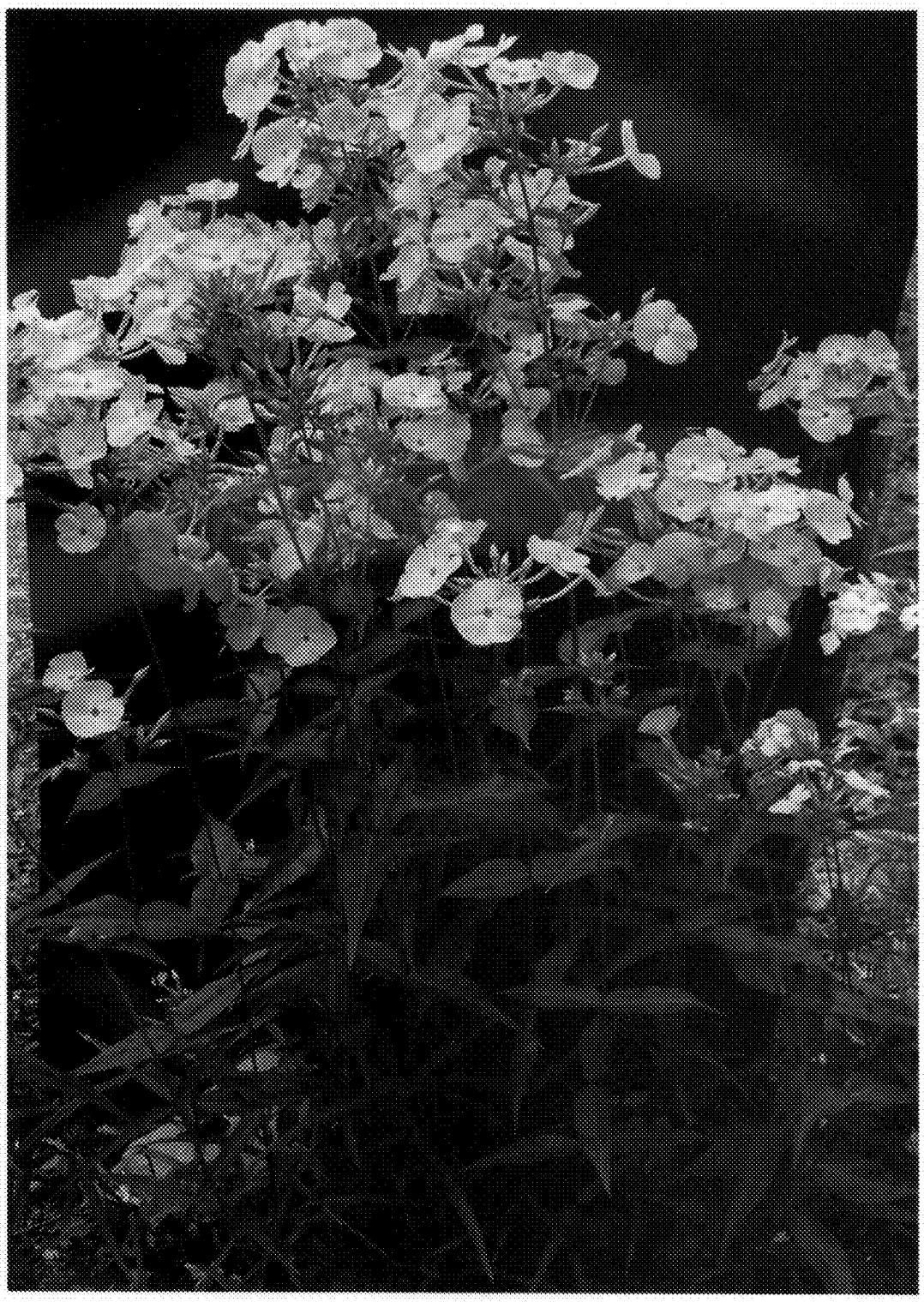

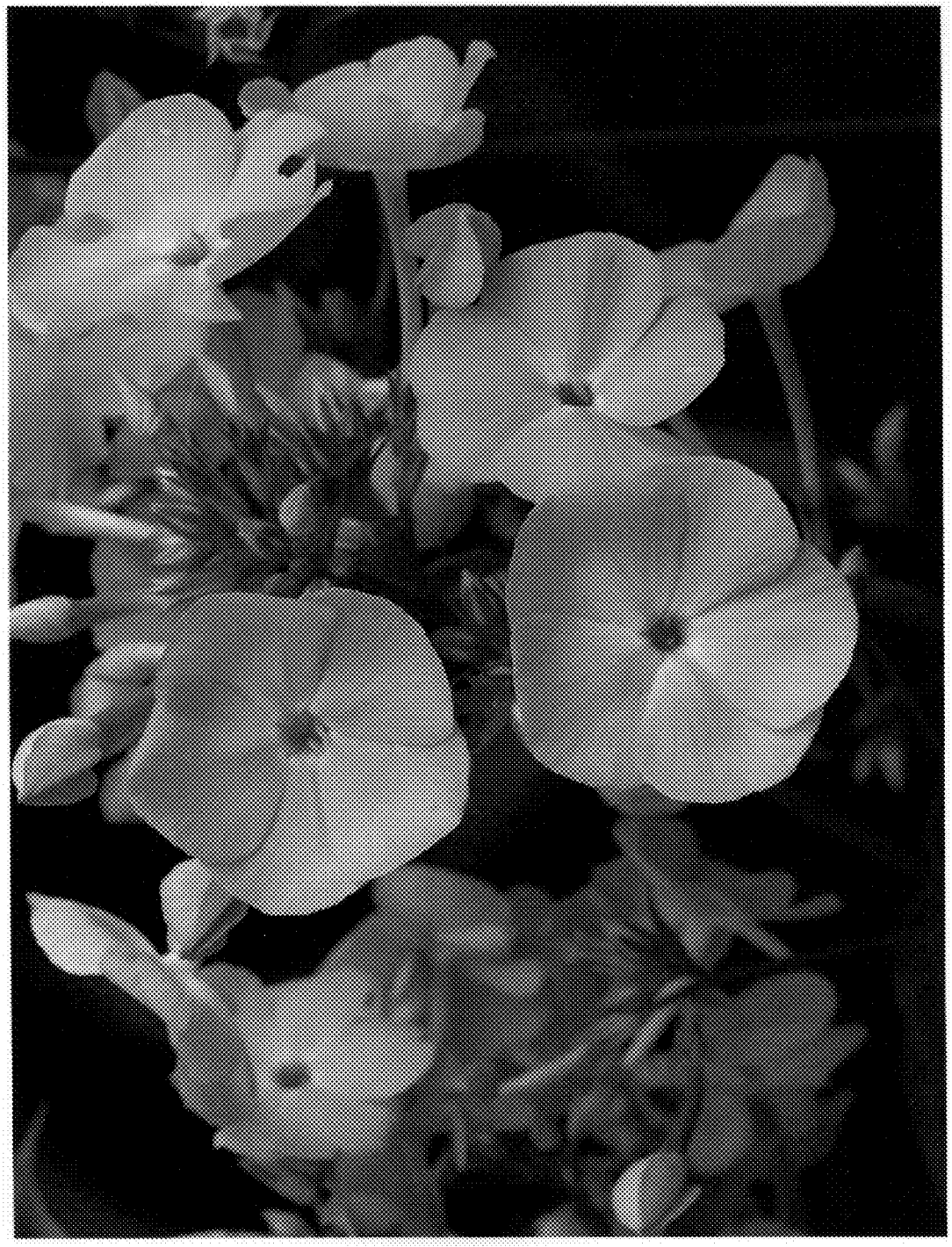

* * * * *